United States Patent [19]
Webster et al.

[11] Patent Number: 5,679,899
[45] Date of Patent: Oct. 21, 1997

[54] METHOD AND APPARATUS FOR NON-DESTRUCTIVE TESTING OF STRUCTURES

[75] Inventors: John M. Webster; Jacqueline M. Mew, both of Forest Hills, N.Y.

[73] Assignee: Holographics Inc., Long Island City, N.Y.

[21] Appl. No.: 398,895

[22] Filed: Mar. 6, 1995

[51] Int. Cl.[6] .................... G01H 9/00; G01H 13/00; G01N 29/12

[52] U.S. Cl. .................... 73/656; 73/657; 73/582; 73/602; 356/347; 356/35.5

[58] Field of Search .................... 73/656, 655, 657, 73/594, 800, 579, 582, 659, 602, 643, 588; 356/349, 35.5, 345, 347, 346, 348; 364/822, 827, 508

[56] References Cited

U.S. PATENT DOCUMENTS

| 3,717,412 | 2/1973 | Takuma et al. |
|---|---|---|
| 4,408,881 | 10/1983 | Clarady et al. .................... 356/347 |
| 4,428,235 | 1/1984 | Sugiyama .................... 73/579 |
| 4,581,939 | 4/1986 | Takahashi .................... 73/643 |
| 4,659,224 | 4/1987 | Monchalin .................... 356/352 |
| 4,871,255 | 10/1989 | Tenjinbayashi .................... 73/656 |
| 5,004,345 | 4/1991 | Hung .................... 356/35.5 |
| 5,086,775 | 2/1992 | Parker et al. .................... 128/660.01 |
| 5,146,289 | 9/1992 | Newman .................... 356/35.5 |
| 5,408,305 | 4/1995 | Webster et al. .................... 356/35.5 |
| 5,410,406 | 4/1995 | Webster .................... 356/347 |

Primary Examiner—Hezron E. Williams
Assistant Examiner—Rose M. Finley
Attorney, Agent, or Firm—Brumbaugh, Graves, Donohue & Raymond

[57] ABSTRACT

A system for non-destructively inspecting or testing for faults or damage in or beneath the surface of structures, such as debonds or delaminations in composite materials, or cracks, broken stringers, delaminations and the like in structures. High energy acoustic impulses are focused onto a sample point or local area for vibrationally exciting the surface of the structure under inspection. A laser Doppler camera system directs a laser beam onto the excited area and derives from reflected light energy information including time domain signals. A Fast Fourier Transform (FFT) is constructed for each sample point and an analysis made to set aside FFTs deviating from a preselected standard which represent damaged or other anomalous areas. The remaining FFTs represent an average or statistical FFT spectrum of the undamaged or fault-free area. The average FFTs and the deviating FFTs are then subtracted to provide a clear and unambiguous signal of the fault and other anomalous areas in the structure under test. This information can then be visually displayed as printouts of a contour map or graph to display faults.

4 Claims, 5 Drawing Sheets

METHOD AND APPARATUS FOR NON-DESTRUCTIVE TESTING OF STRUCTURES

BACKGROUND OF THE INVENTION

This invention relates to improved detection and analysis of faults such as debonding and delamination faults in composite materials and structural faults in monocoque and semi-monocoque structures or other structures, when such faults are located through use of non-contacting high intensity acoustic impulse excitation of the structure and the resulting excitation of the structure is interrogated by a scanning laser Doppler vibrometer.

Advances in modern composites have made it possible to introduce high strength/weight ratio materials into highly stressed critical components such as those used in aircraft and weapons, for example. The development of alternative resin systems has also greatly improved the flexibility of manufacturing such structures. Tough, high strength, high temperature thermoplastic polymers combined with advanced graphite fibers have made it possible to consider structures of a size and strength heretofore considered economically impractical. In the aircraft industry, for example, where composite materials are increasingly being used, the size of composite structures range from relatively small control surfaces on drones, targets and missiles to the very large surfaces of vertical stabilizer, aileron and wing control elements on military and commercial aircraft; future applications include fuselage structures.

Such composite materials have failure modes quite different from metals and alloys in that they suffer from delamination, debonding and cracking, as well as deterioration from fatigue and ambient exposure. In addition to failure in service, these materials may also suffer from defects in manufacturing similar to those which occur under field stresses. Thus, a practical technique is needed for non-destructively locating faults in composite structures which is suitable not only for in-plant non-destructive evaluation but for field use as well.

Among known techniques for detecting delamination or debonding is that known as acoustic "scrubbing" wherein a small instrument containing an acoustic crystal is manually scanned across the surface of the object under examination while electronically "listening" for anomalies in the reflected acoustic wave. For small objects, this process is simple and efficient, but is much too time-consuming, and therefore prohibitively expensive, to be practical for evaluation of large components and structures.

Another suggested technique is to heat part or all of the surface of the component by flash discharge lamps and after a predetermined delay make an infrared photograph of the surface with a CCD camera system. This system is premised on the assumption that decay of the surface temperature during the delay period is a function of the thickness and thermal conductivity of the material, factors which would be affected by debonds or delaminations and cause anomalies in the photograph. The effectiveness of this system is highly dependent on the surface finish or condition of the object.

Perhaps the simplest, yet most effective, technique that has been proposed is to simply tap the surface of the structure at different spots and listen to the resulting sound; a dead or hollow sound indicates a fault condition, as opposed to a sharp sound in a fault-free area. This technique, too, is very time-consuming and the evaluation is very subjective, making it impractical for evaluation of most structures.

Faults occurring in monocoque and/or semi-monocoque structures, basically a skeleton over which a skin is secured and of which an aircraft fuselage is a practical example, are manifested in much different ways than in composite structures. If the skin develops cracks, or is weakened or becomes detached from the skeletal framework, then a rupture can result causing impairment of the entire structure, particularly if it is an aircraft fuselage which is usually pressurized. Similarly, if the underlying skeletal structure cracks, or becomes corroded, or the fastening system fails, structural failure can result.

The difficult task of inspecting the substructure of the skin of an aircraft fuselage for corrosion, broken fastenings, cracks or loose rivets is effectively performed by the method described in applicant Webster's copending U.S. patent application Ser. No. 08/011,911 filed Feb. 1, 1993 now U.S. Pat. No. 5,410,406. The therein disclosed non-destructive inspection method includes the steps of mechanically exciting, with an exciter affixed to the object, a vibrating nodal pattern in the outer skin of a monocoque structure, panels of which may freely vibrate at resonant frequencies. The frequency of excitation is scanned through a spectrum which includes such resonant frequencies and is locked onto a resonant frequency which is uniquely characteristic of a certain phase relationship of the anti-nodes of the nodal pattern. The amplitude of the excitation is then varied until the anti-nodes of the pattern are optimized to be either bi-concave or concave/convex, and when such optimization occurs, two time-displaced holograms of the vibrating outer skin are recorded in synchronism with maximum plus and minus displacement, respectively, of an anti-node. It is from this fringe map of contour patterns, which is uniquely characteristic to any given structural condition, that faults are interpreted.

The speed and accuracy of analysis of the results produced by this vibrational technique for detection of flaws is improved by the system described in U.S. patent application Ser. No. 08/108,123 filed by both the present applicants on Aug. 17, 1993, now U.S. Pat. No 5,408,305 the disclosure of which is incorporated herein by reference. It is a computer-based system which analyzes nodal patterns induced in the surface of a structure being inspected either by analyzing a record obtained by interferometry, or by directly scanning, or digitally interrogating point-by-point, the vibrating surface of the structure with a beam of quasi-coherent radiant energy and, utilizing the Doppler effect, reading the out-of-phase displacement of the surface to produce a visual contour map of the surface for capture and computer analysis. Alternatively, a computer may be programmed to either directly capture the nodal pattern and provide either a direct readout of the location and/or identity of faults, or directly capturing the nodal pattern for later processing.

A still further improved technique for detecting and locating faults in composite materials employs a non-contacting high energy acoustic impulse focused onto a local area for vibrationally exciting the surface of that area, as described in applicant Webster's copending U.S. patent application Ser. No. 08/157,815, filed Nov. 24, 1993, now U.S. Pat. No. 5,505,090 the disclosure of which is incorporated herein by reference. In that system, a laser Doppler camera system directs a laser beam onto the excited area and derives from light energy reflected back from the excited area, the velocity of out-of-surface displacements from which is derived, relaxation frequencies generated by the surface of the excited area, and provides an indication as to whether a fault is present in that area. The non-contacting acoustic device produces pulses and with the laser beam is directed to successive local areas in synchronism, according to a point by point scanning pattern, at each of which local areas the reflected light is analyzed. The acquired data is then processed and visually displayed in a manner which indicates the presence of a fault and its location to enable an operator to analyze the data further and ascertain the type and extent of the fault.

In that technique a limited number of frequencies are normally recorded, for example, up to twelve in number, each preselected by the operator who also selects the band width of the particular recorded frequency. This data is recorded at each scan point. The problem has been found to lie in knowing which frequency or set of frequencies is actually recorded and uniquely represent the damaged and undamaged areas.

It has been found that the relaxation frequency spectrum produced by sonic wave excitation of undamaged structural areas in the previous system is sometimes difficult to distinguish from the spectrum produced by damaged areas. This problem is compounded by the fact that the signature or relaxation frequencies peculiar to any specific fault condition vary not only from material to material but from one fault condition to another if the physical characteristics of the faults differ. Therefore there is a need for an analysis technique that will clearly delineate faulty structural areas from each other as well as from undamaged structural areas.

SUMMARY OF THE INVENTION

In order to overcome the above difficulties, the present invention takes advantage of the fact that proportionally large areas, usually the greater area of the object undergoing non-destructive testing, will be undamaged or fault-free although its underlying structure may differ in the frequencies exhibited across the surface because of the presence of such items as supporting structural members. Thus assuming that the structure of the object is fault-free, all sample points or local areas on any particular object should exhibit somewhat similar relaxation frequency spectra and signal amplitude, varying only because of its local characteristics, which normally will be known. However, because of slight variations inherent in any structure, some statistical comparison will be necessary to obtain a representative average spectrum of the relatively large undamaged area of the structure being examined. As described in Webster's copending U.S. application Ser. No. 08/157,815 (now U.S. Pat. No. 5,505,090), the detection and location of a fault or damaged area depends upon the faulty area of the object exhibiting a relaxation frequency and signal amplitude, or number of such frequencies or signal amplitudes, which differ from that of a normal undamaged area.

Whereas in the previous techniques only a limited prescribed number of particular relaxation frequencies were able to be recorded and then only of a prescribed bandwidth, it is now possible to record substantially an entire spectrum and construct a Fast Fourier Transform (FFT) of each local area. It is a part of the invention that after recording the spectrum from each sample point or local area, each point of the scan is compared to the others in order to determine which are in damaged or faulty areas. Note that fault-free areas will tend to exhibit very similar characteristic relaxation frequencies and signal amplitudes, and will usually be the majority of the points. On the other hand, if the points are in a damaged area, or above a faulty substructure, the relaxation frequencies and signal amplitudes will differ. If necessary subsequent scans may be taken of a suspect area so that more detailed information can be collected.

In order to differentiate between the relaxation frequencies and amplitudes from damaged and fault-free areas, the data collected from each point from the sonic wave excitation is subjected to Fast Fourier Transform (FFT) analysis. The FFTs are processed by computer analysis and those that are different and thus deviate from a preselected standard are set aside in the computer and stored. FFT's that remain will have a high probability of representing the fault-free area and an average of those is a statistical representation of the FFT spectrum of that relatively large area. In other words, an analysis of those remaining FFTs within the preselected standard is made to obtain such average or statistical spectrum of the undamaged area. Those FFTs which were set aside (which may include those from known supports such as stringers) and the average or statistical FFT, are then subtracted from each other and the resulting signal which remains represents the damaged area. It should be noted that any damaged area may exhibit a rather different spectrum at any cluster of sample points within the damaged area, i.e., there may well be several different spectra representing a damaged area, but all differing from the average or statistical spectrum of the undamaged area. These can be processed sequentially to provide signals used to construct a visually displayed contour map.

BRIEF DESCRIPTION OF THE DRAWINGS

The file of this patent contains one sheet of drawings executed in color. Copies of this patent with the color drawings will be provided by the Patent and Trademark Office upon request and payment of the necessary fee.

The advantages and features of the invention will become more apparent when the following description is read in connection with the accompanying drawings, in which.

DESCRIPTION OF THE PREFERRED EMBODIMENT

Figure 1:
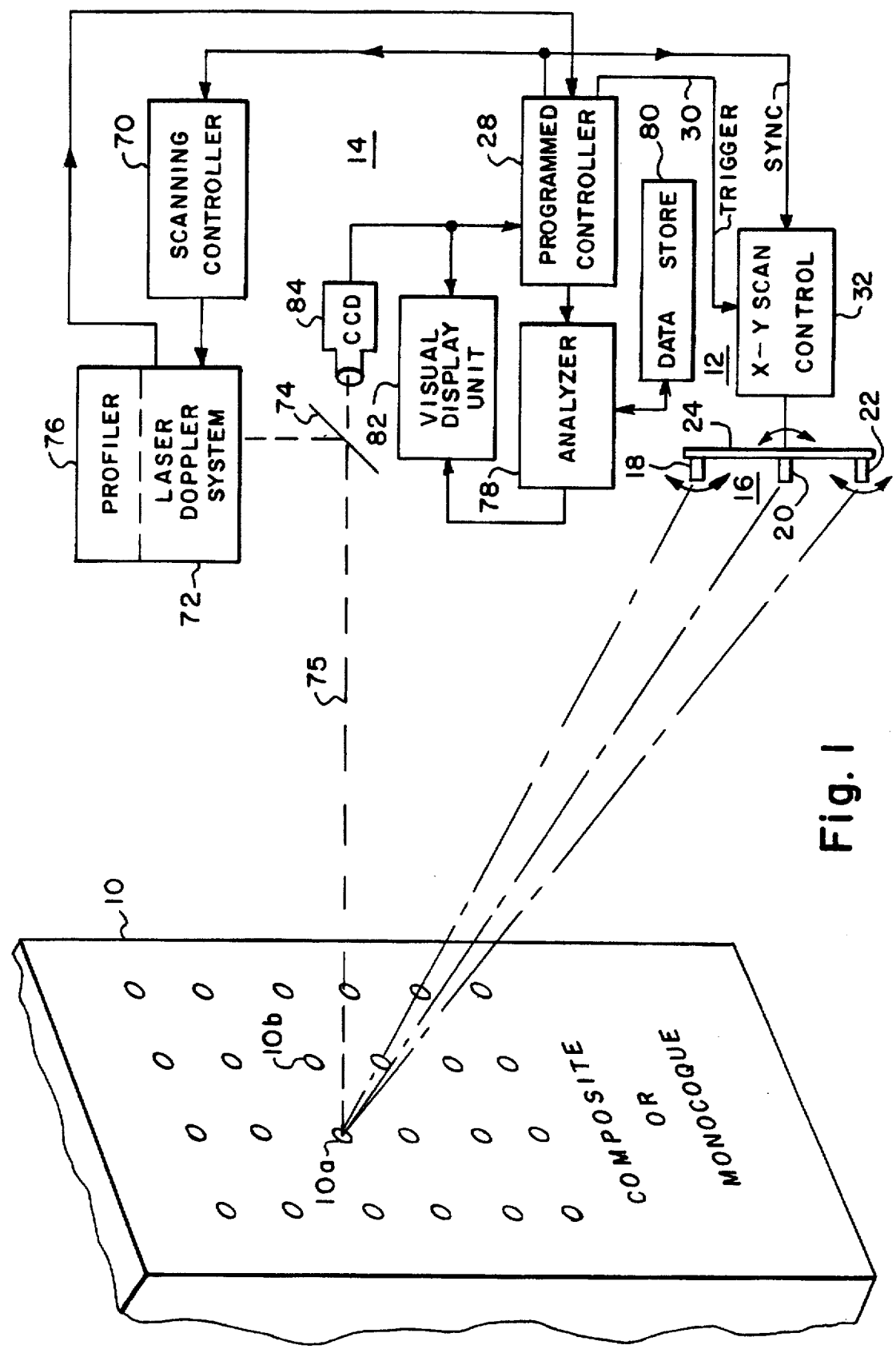
FIG. 1 is a diagrammatic block diagram (partially schematic) of a system for non-destructively inspecting a structure, as set forth in applicants' earlier application.

FIG. 1 is a diagrammatic block diagram of a system for performing substantially quasi-real-time analysis of structural faults in an object or structure 10, which may be a section of any materials including metallic honeycomb, composite materials or a monocoque or a semi-monocoque or other structures, as fully set forth in applicant Webster's copending U.S. application Ser. No.08/157,815 (now U.S. Pat. No. 5,505,090). The system consists of two basic subsystems: a system 12 located remotely from the structure for vibrationally exciting the surface point-by-point with acoustic pulses; and a laser Doppler system 14 which scans the surface of object 10, in synchronism with the point-by-point scanning of the acoustic pulses, for measuring out-of-plane surface displacement of successive points and providing a visual display of the location and extent of any structural faults.

For simplicity of illustration, a supporting structure 24 is shown somewhat remote from the laser doppler system 14. However, it should be understood that the systems 12 and 14 are preferably closely spaced with the supporting structure 24 generally parallel to the plane of the tested object 10. Note also that the acoustic pulses generated by discharge devices 18, 20 and 22 travel substantially unidirectionally from the devices as described in more detail below.

Considering first the remote acoustic pulse generating and scanning system 12, described in detail in copending Application Ser. No. 08/157,815 (now U.S. Pat. No. 5,505,090), a high energy acoustic shock-wave is focused onto a localized area or sampling point 10a on the surface of object 10 by an array 16 of discharge devices, mounted on a suitable supporting structure 24. The array 16 may comprise any number of discharge devices, for example, with four of them equally spaced along a circle and a fifth supported at the center of the circle, as shown in copending Application Ser. No. 08/157,815 (now U.S. Pat. No. 5,505,090). Three of the five discharge devices are visible in FIG. 1 at 18, 20 and 22. As indicated by the arrows adjacent devices 18 and 22 in FIG. 1, the supporting structure 24 includes means such as motors (not shown) for controlling the structure 24 and for controlling the distance and directivity axis of the discharge devices so as to variably focus them (as shown by arrows) at a point along the Z-axis so that acoustic pulses produced simultaneously by each discharge device of the array converge at the same point on the surface of the test object at the same time. This adjustability of the focal point of the array allows the system to inspect an object over a range of distances from the object. Each of the discharge devices synchronously generates high energy acoustic pulses of short duration, for example, less than 1 µsec. at source, to several milliseconds, at a predetermined repetition frequency, typically 100 pulses per second although far higher frequencies in the kilohertz range can be used, under control of trigger pulses supplied from a programmed controller 28 via line 30 and applied to the arrayed discharge devices through an X-Y scan control system 32. The scan control system scans the focal point of the array 16 over a selected area of the test object according to a predetermined pattern, typically horizontally and vertically as indicated, in stepwise fashion, for example, from small area 10a to small area 10b, etc. The discharge devices are triggered at the correct moment so that an acoustic pulse is launched to cause the acoustic wave to impinge on a desired area or sampling point 10a, for example. The X-Y scan control system 32 is preferably electrically controlled from a range finder system (not shown) to insure that a sharp focus at each sample point on the object is obtained as the distance from the array changes as the array is tilted during scanning. Each focused acoustic shock-wave excites a local area 10a, 10b, etc. of the surface of the object in a manner closely simulating that produced by "tapping" with an implement such as a rod or pencil, producing, following the pulse, relaxation frequencies and signal amplitudes having characteristics uniquely indicative of the presence of a rupture or fault.

It is essential to the operation of the system that the duration, bandwidth and frequency of the acoustic wave impinging on the structure under test be much less than the relaxation frequencies or relaxation characteristics of the material or structure being tested, including the fault areas.

Before describing the laser Doppler portion of the system, the phenomena produced when the surface of a test object is "tapped" with an acoustic pulse or wavefront will be briefly summarized. If a damaged area of a composite material, for example, is tapped, there is a change in the tap noise from what is heard when a fault-free area is tapped, which indicates that the surface of the material moves differently where there is damage than where the material in the region of the tap is free of damage or fault. Furthermore, in the vicinity of a fault, whether it be on the surface or internal, following excitation by the "tap", the material exhibits relaxation frequencies which are different from those exhibited by a fault-free area of the composite material. A crude analogy might be the way an imperfect bell rings down or rings up in frequency after being struck. Differences in out-of-plane displacement amplitude or frequency between damaged and fault-free areas, i.e., signal amplitudes and differences in relaxation frequencies exhibited by damaged and fault-free areas, both of which are excited by "tapping" the surface with remotely generated acoustic pulses, are both relevant and are utilized to ascertain the location and extent of faults.

Reverting to FIG. 1, under control of a scanning controller 70, itself controlled by programmed controller 28 and synchronized with the X-Y scan control 32, a laser Doppler camera system 72 directs a laser beam, i.e., a beam of coherent light, onto a beam splitter 74 and scans a beam 75 over a selected area of interest of the test object 10 in unison with the scanning of acoustic pulses. Accordingly, as each point 10a, 10b, etc. on the surface of the object is excited, that is, "tapped" by an acoustic pulse, it is simultaneously being illuminated by a narrow or focused laser beam. Light reflected back from the illuminated point is directed by beam splitter 74 onto laser Doppler camera 72 which detects shifts in wavelength of the reflected light caused by out-of-surface displacement of the excited area from which the light was reflected, the shifts in wavelength being indicative of whether or not a fault is present in that area of the test object. On the basis of such shifts in wavelength, laser Doppler camera 72 provides a color printout which indicates by different colors or monochrome tones the velocity of movement of the excited area on the surface of the test object. In this display, surface displacements at very low velocity are represented, for example, by blue areas, and greater movement is represented by areas of red and purple; a purple area depicts a velocity of surface movement of 5 millimeters per second. Progressively higher velocities are represented by green and yellow, the latter depicting a velocity of movement up to 8 millimeters per second. While meaningless in themselves, the colors are representative of the surface movement and the surface changes that are actually occurring as a result of being vibrationally excited by an acoustic pulse, as explained in copending application Ser. No. 08/157,815 (now U.S. Pat. No. 5,505,090).

To insure that a given displacement of a point on the surface of the test object is similarly displayed by the laser Doppler camera, regardless of where on the surface the point is located, or whether the surface is planar, or at some angle or curved, a profiler 76 can be interfaced with the laser Doppler camera 72. The principle of operation of profilers is well known, and they are used in many applications, including, for example, medical. The profiler may comprise a scanning laser system or a scanning acoustic system incorporated either in the head unit or casing of the Doppler camera or immediately adjacent to it. The purpose of the profiler is to provide information to the Doppler signal analyzing computer of the angle of the exact spot on the object surface which is being interrogated by the Doppler system at any precise moment. This information enables the analyzer to compute the correct surface displacement amplitude, including the amplitude and the relaxation frequencies for that spot. In other words, correct out-of-plane amplitude can only be calculated if the angle of the surface with respect to the camera axis is known. It is also necessary to mount the Doppler camera system on a relatively stable platform in order to maintain beam pointing stability. For example, although currently available laser Doppler equipment will operate satisfactorily on a surface not isolated from ambient vibrations, in many of the situations in which the present apparatus is intended to be used, say, carried in the slightly swinging basket of a "cherry-picker" for gaining access to the fuselage of a large aircraft, unless stabilized the narrow laser beam projected from the Doppler camera would also swing wildly and the information contained in the signal reflected back into the camera would be useless.

Under control of included software, controller 28 supplies relevant data from Doppler camera 72 to an analyzer 78 in which acquired data is compared with information stored in a data storage device 80 regarding surface displacement and relaxation frequencies previously measured on a similarly excited fault-free structure constructed of the same material. Such comparison locates fault points and identifies relaxation frequencies with a view to analyzing the extent and type of the fault. The relaxation frequencies may be recorded and analyzed during a scan of the selected area, or may be recorded for subsequent analysis, after the location of a fault has been ascertained, by analysis of only data derived from the out-of-plane of-plane displacement of the excited areas.

Summarizing, programmed controller 28 interfaced with the laser Doppler camera 72 retains in memory, data relating to both the amplitude of surface displacement and details of the relaxation frequencies exhibited by the interrogated area of the object, including spatial information which defines its location, so that an area exhibiting any fault conditions can later be re-interrogated. This can be achieved either by relocation and individual re-examination of the selected area, or by processing the information with data stored in the memory of the computer during the initial scan.

The computer 28 displays the acquired data on a visual display unit (VDU) 82, superimposed on a picture of the object collected by a CCD camera 84, in the form of a colored contour map of the fault area or, alternatively, by another form of marking wherein the essential data analysis of the fault area is displayed on either the same or a linked VDU or printout system. The acquired data may be displayed in quasi-real-time, or held in store for display immediately following the interrogating scan.

With suitable modification of its software and incorporation of a laser profiler, the laser Doppler system 72 and associated signal processing hardware and software may be implemented with commercially available equipment such as the PSV-100 scanning laser Doppler velocimeter, also known as a vibrometer, marketed by Polytec Optromics Inc. of Auburn, Massachusetts or a similar system marketed Ometron of Sterling, Va., both companies providing scanning Doppler velocimeters which can be operated with suitable computer software. Thus this non-contact, full-field system for vibration measurements combines a laser Doppler vibrometer with a fast scanning system, signal processing circuitry, a high performance computer, video graphics and software specifically developed for rapid, automated vibration measurement and analysis. The software controls the entire measuring system, including high speed signal processor, A/D converter, laser focus and position, vibrometer electronics and video system, and is modified in the present system to also synchronize scanning of the acoustic pulses with that of the laser beam and to provide synchronization to the discharge devices at times such that acoustic pulses are produced at an optimum time with respect to the time the Doppler vibrometer beam is interrogating the same local area on the surface of the test object.

While in the system shown in FIG. 1 the acoustic pulse and laser beam are stepped or continuously scanned covering scanned areas or sample points 10a, 10b, etc. at a rate of possibly up to 100 points per second with existing technology, it is possible to scan the surface at higher rates. For example, the computer of the Polytec Optromics laser vibrometer system has only enough power to scan and analyze about 100 samples per second which, coupled with the finite duration of the acoustic pulses and the interval between them, dictates the scanning operation; also there are at present limitations on the mirrows controlling the laser scan. When computers having increased power are developed, which can be expected in view of past history of computer development and the optical system further developed, it should be possible to increase the sampling rate of the laser Doppler system so as to examine more rapidly areas of the test object. There may be a top limit on the sampling rate, however, imposed by the duration (i.e., "ring time") of the relaxation frequencies following each interrogating acoustic pulse during which such frequencies must be sensed and analyzed.

The above-described concepts and principles are equally applicable in the inspection of many materials which may contain hidden faults such as composite materials, metallic assemblies, monocoque or semi-monocoque structures or objects of other forms; the display of faults may differ from one type of structure to another, but once it has been determined how a particular type of fault is manifested in the display for different types of structures, the acquired displacement and relaxation frequency data that produced the display can be used as a frame of reference for identifying a fault and its extent in a like composite material and/or structure. For example, just as in the method described in the aforementioned copending application Ser. No. 08/011,991 (now U.S. Pat. No. 5,410,406), in which excitations of the outer skin of a semi-monocoque structure at a particular frequency and amplitude produces an anti-nodal pattern uniquely characteristic of one of several potential types of faults, both surface and subsurface, acoustic excitation of the outer skin of the same structure will generate a combination of surface displacement and relaxation frequencies which when analyzed and displayed will present a pattern also unique to that type of fault.

It has been found, however, that relaxation signatures or background "fingerprints" representative of the undamaged area of the structure under test are often visually indistinguishable when compared with relaxation signatures from the damaged areas even when a time domain trace, such as provided by the analyzer 78 to the visual display unit 82, is processed to a Fast Fourier Transform (FFT) by a Fast Fourier Transform Analysis System.

Figure 2A:
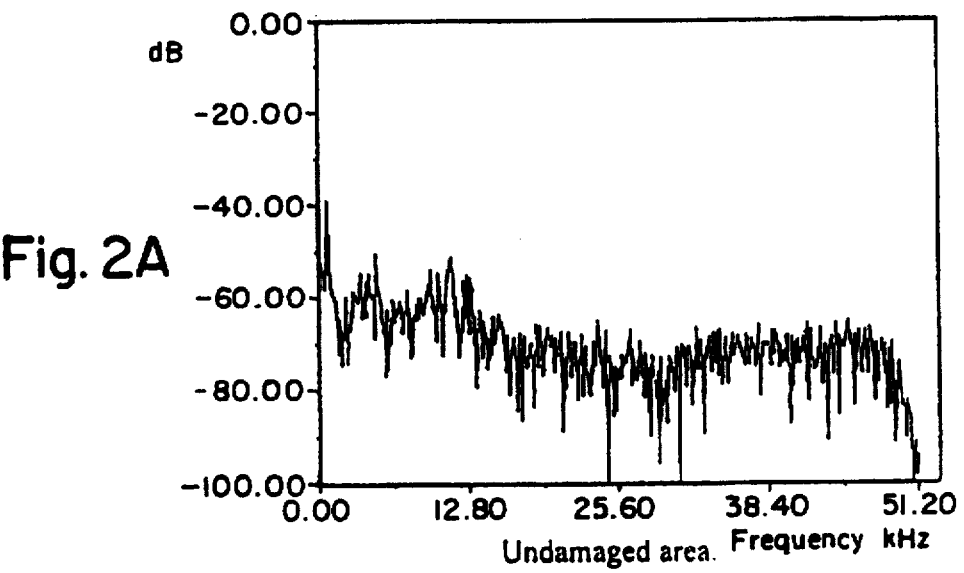
FIG. 2A, 2B and 2C show shows three graphs of recordings of Fast Fourier Transforms (FFTs) taken from single data points of an aluminum honeycomb composite sample provided by the system of FIG. 1.
Figure 2B:
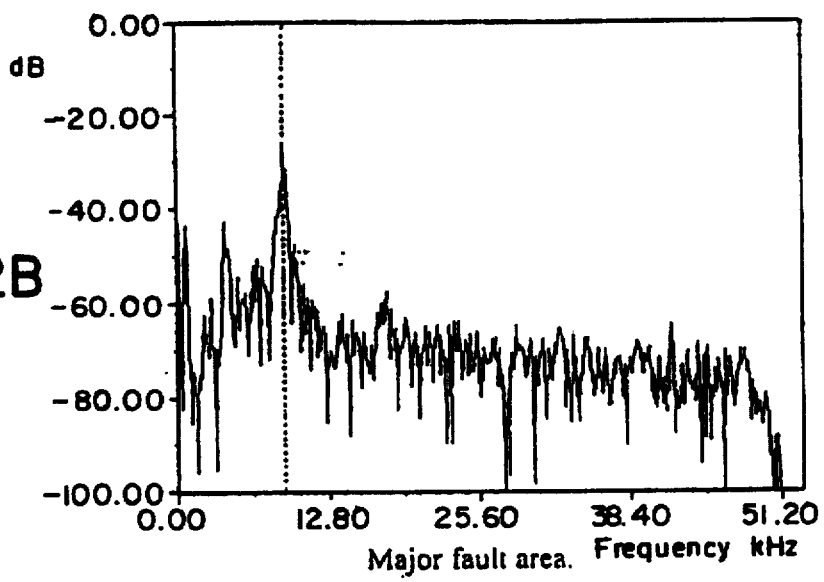
Figure 2C:
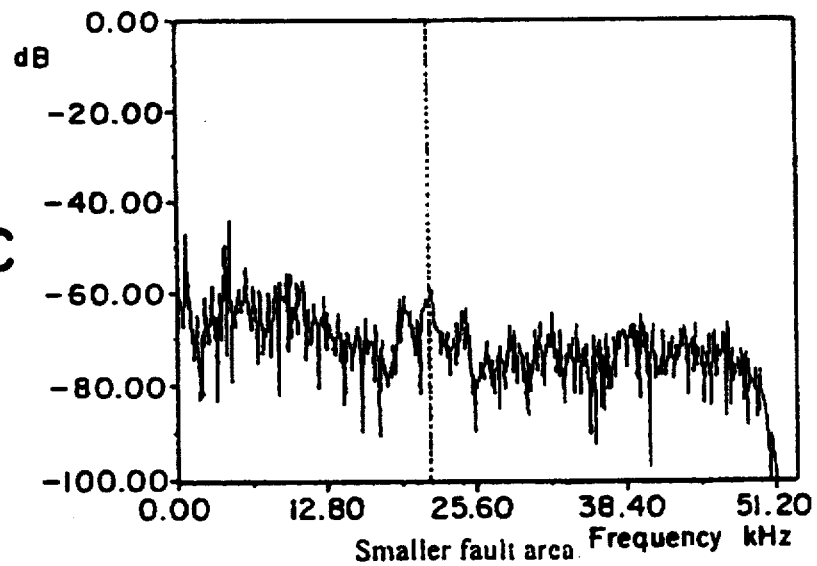

The graphs of FIG. 2A, 2B and 2C show examples of FFTs, frequency spectra provided by the Fast Fourier Transform Analysis 91 (FIG. 3), from various points on a structure of aluminum honeycomb 2¾ inches thick bonded to a pair of ⅛ inch thick aluminum sheets used in aircraft construction. The FFT of a point on an undamaged area is compared with the FFT of a point on a major fault area, a debond of the upper skin from the honeycomb about one inch in diameter, indicated by the vertical dotted line. The lower graph FIG. 2C shows an FFT of a somewhat smaller debonded area also indicated by a dotted line. Note that the differences between the major fault area and the undamaged area are clearly and obviously portrayed by visually comparing the two upper graphs, FIGS. 2A and 2B, in accordance with the technique described in applicant Webster's copending U.S. application Ser. No. 08/157,815 (now U.S. Pat. No. 5,505,090). The lower frequency and high amplitude spike (marked by a dotted line) is clearly visible on the major fault FFT spectrum.

In contrast, as the fault decreases in size, its relaxation frequency characteristics and amplitude, or signature, are not very obvious and, in fact, will eventually disappear into the background frequency noise as the fault diminishes in size or depth. Thus in the lower graph of FIG. 2C, the smaller fault area, marked by the dotted line on its FFT, is difficult to identify positively as a fault, when comparing the undamaged and smaller fault area FFTs.

In order to provide an unambiguous record of faults, and especially small damaged areas, in accordance with the present invention the background noise that interferes with identification of such faults is minimized, as explained below.

Figure 3:
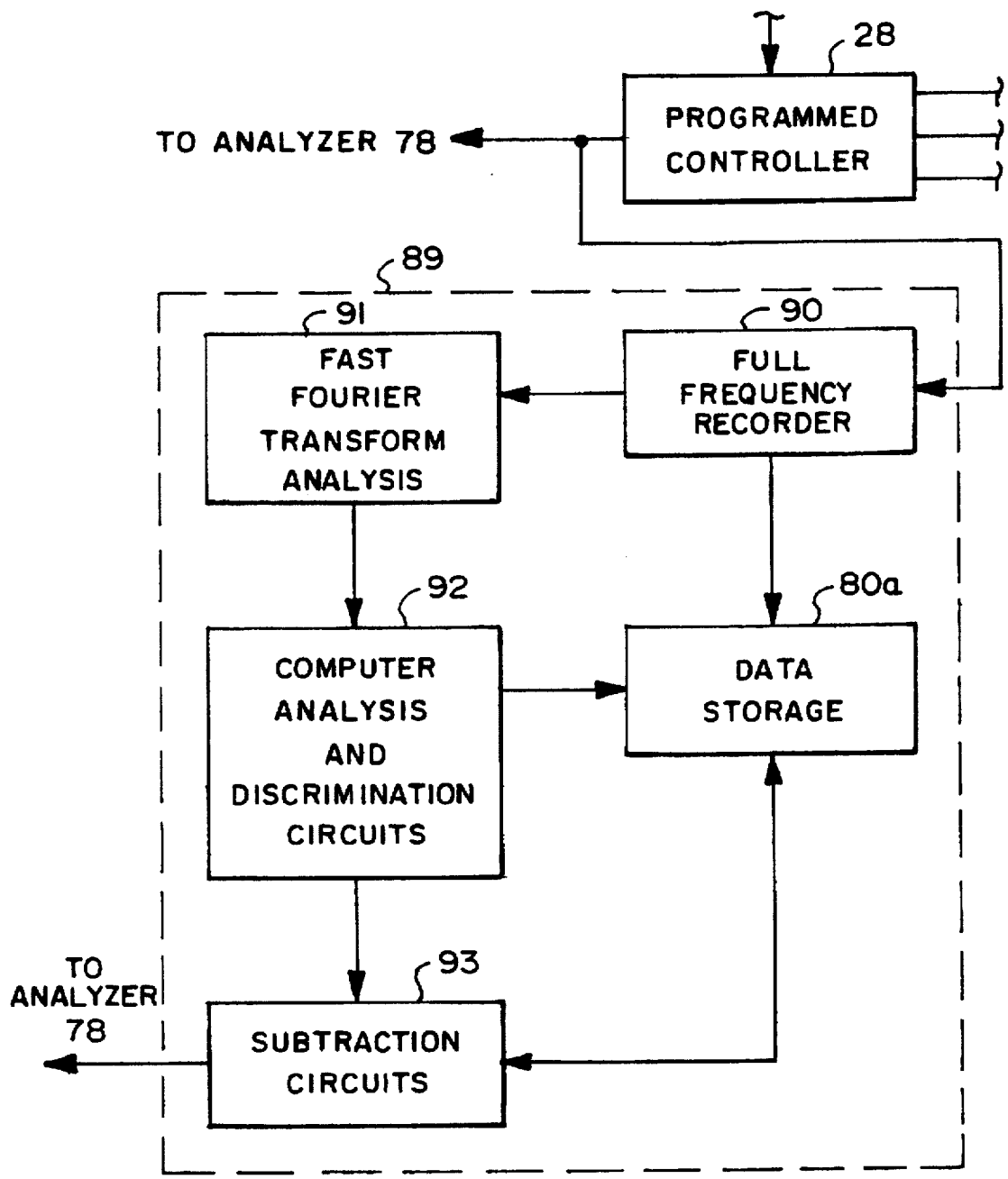
FIG. 3 is a diagrammatic block diagram of a portion of an improved system for non-destructively inspecting a structure used with the system of FIG. 1.
Figure 4:
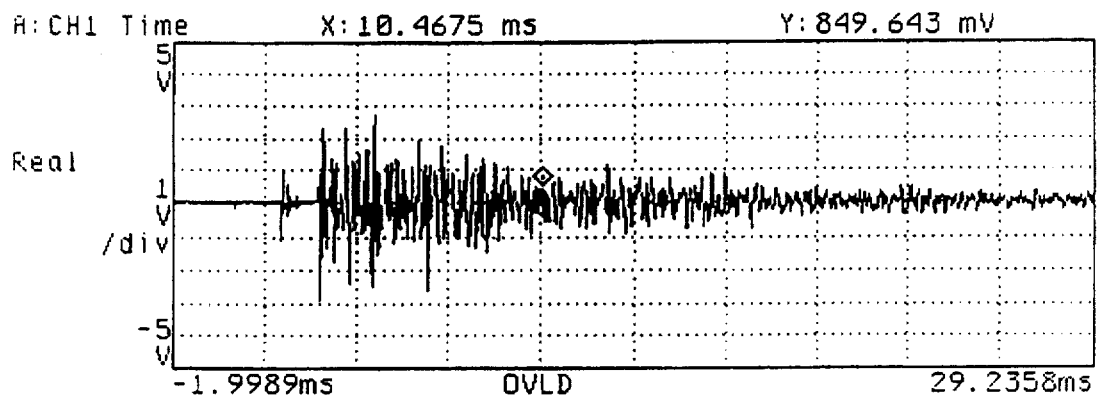
FIG. 4 is a graph of signals representing a time domain or signature taken from an aluminum honeycomb sample prior to processing to an FFT.

At the outset, FIG. 3 shows computer and logic circuits 89 which when used with the system of FIG. 1, provide the benefits of the invention. It is desirable in the inventive system to record substantially all frequencies received and provided as time domain signals by the Laser Doppler System 72. To this end, the Full Frequency Recorder 90 receives time domain signals from the Laser Doppler System 72 (through the controller 28) of FIG. 1 to provide a time domain recording exemplified by the graph of FIG. 4. Note the decay of the recorded signals with time.

Figure 5:
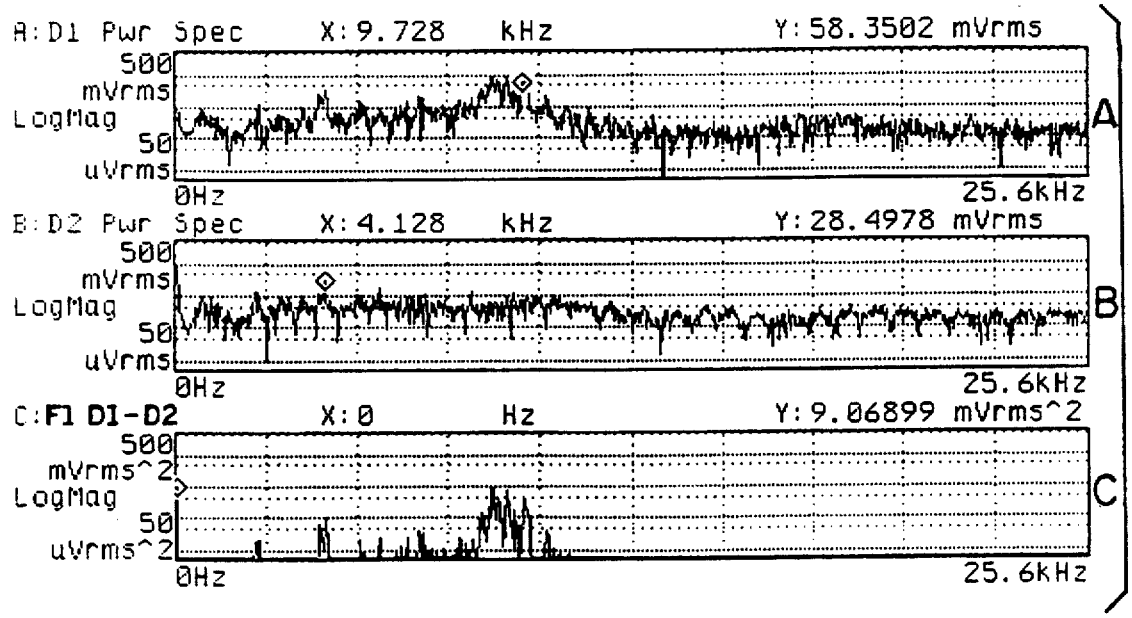
FIG. 5 shows three graphs of FFT spectrum taken from scanned grid points on aluminum honeycomb.
Figure 6:
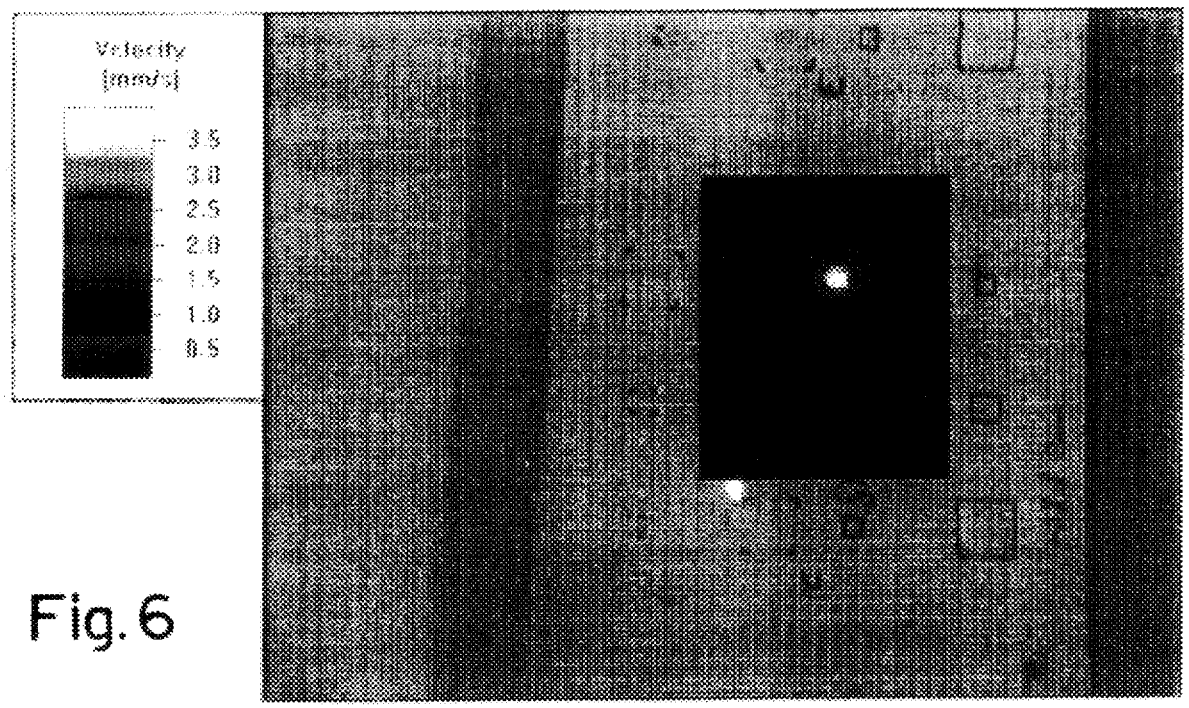
FIG. 6 is a color printout of the inventive system illustrating in a top view how a fault in a tested structure can be shown visually as a contour map using the FFT subtraction technique.
Figure 7:
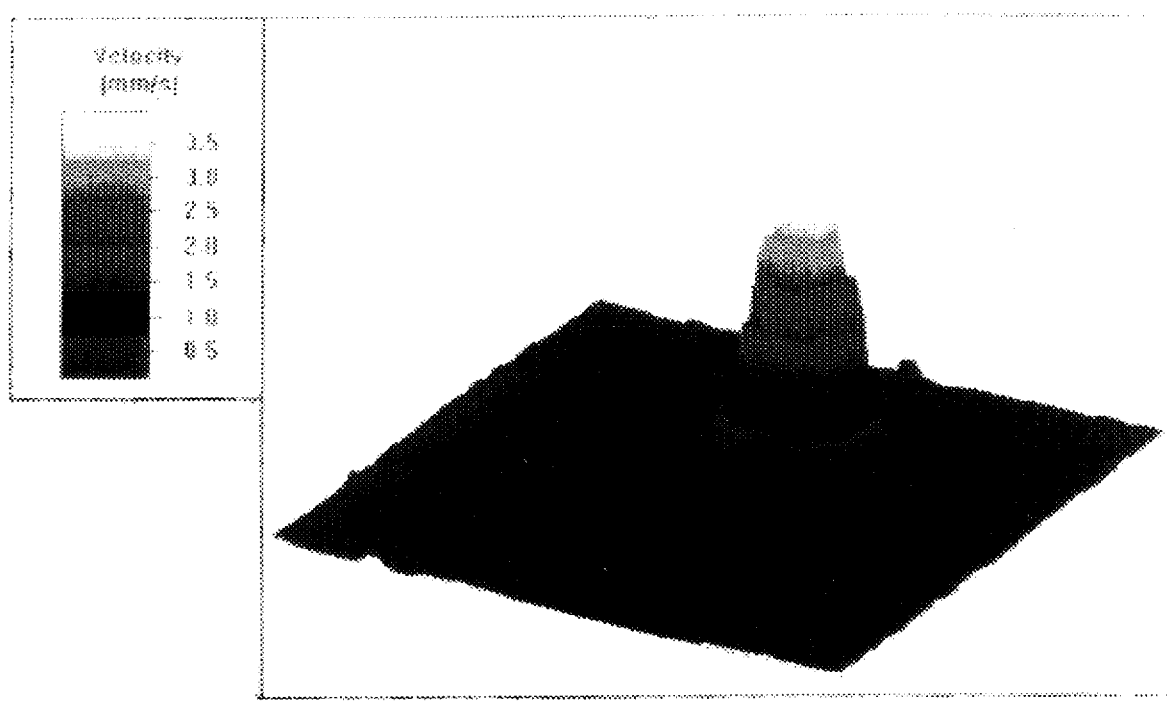
FIG. 7 is a color printout similar to FIG. 6 but in a perspective view.

To explain the basic concepts of the invention with reference to the graphs of FIG. 5, local areas or points on the scanning grid on a specimen of aluminum honeycomb, with a known defective area, when scanned provide time domain signals to the Fast Fourier Transform Analysis 91, which outputs the FFT spectrum similar to that shown as graph A in FIG. 5. Further points scanned on the same sample, but from a fault-free area, provide an FFT spectrum from FFT Analysis 91 like that shown in graph B of FIG. 5. After analysis in Computer Analysis and Discrimination Circuits 92, as explained below, FFTs A and B are subtracted in Subtraction Circuits 93 to provide graph C signals, which clearly show the spectra or relevant frequencies and amplitudes which are unique to the damaged area, and can be the basis for a contour map such as shown in FIGS. 6 and 7.

Note that whereas previously only a limited number of particular relaxation frequencies were normally recorded, and those frequencies only over a prescribed bandwidth, the present invention contemplates recording virtually an entire spectrum of frequencies (less unwanted frequencies generated by the ambient environment) to construct a Fast Fourier Transform (FFT) of such frequencies recorded at each sample point.

In further explanation, referring to FIGS. 1 and 3, the system of FIG. 1 is modified to provide the inventive system by supplying the output from the Laser Doppler System 72 through the Programmed Controller 28 to the Computer Logic Circuits 89 which includes computer and logic circuits as well as the FFT analysis.

More particularly, the Recorder 90 records time domain signals from the Doppler System 72 and supplies information to Data Storage 80a (to prevent loss of any useful data) and also to Fast Fourier Transform Analysis 91 to provide FFTs. Then the FFTs are provided to Computer and Discrimination Circuits Analysis 92 which are coupled to Data Storage 80a and Subtraction Circuits 93. The Subtraction Circuits 93 are also coupled to the Data Storage 80a to preserve data for subsequent use. Output signals from the Subtraction Circuits 93 are then supplied to the Analyzer 78 to provide the visual display on the Visual Display Unit 82.

Examining the operation of the inventive system, note that all of the FFTs from the Fast Fourier Transform Analysis 91 are analyzed in the Computer Analysis and Discrimination Circuits 92 to ascertain the average or statistical spectrum of the fault-free area of the specimen under test, which could appear similar to the single point spectrum of Graph B of FIG. 5. This analysis can readily be made by setting aside those FFT spectra deviating from a preselected standard, for example, FFT spectra below a predetermined or preset amplitude level or containing different frequencies. Note that such FFTs will include not only damaged areas but also other anomalous areas including supporting structures such as stringers and the like. The remaining and usually dominant FFTs selected by the discrimination circuits in Circuits 92, are averaged by the Computer Analysis and Discrimination Circuits 92 and furnished to the Subtraction Circuits 93 as an average spectrum (FFT) representing the fault-free area. Those FFTs which deviated from a preset amplitude and frequency standard, for example, the FFTs comparable to Graph A of FIG. 5 and FFTs representative of other features of the structure under test, such as supporting members and the like, are set aside in the Data Storage 80a. The set aside FFTs representing the damaged areas and supporting structure, or the like, are supplied to the Subtraction Circuits 93, which include standard mathematical circuits, to subtract the average or statistical background FFT spectrum, and the damaged area FFT's, to provide a resultant signal comparable to that illustrated by the Graph C of FIG. 5, clearly depicting a damaged area. In the manner explained heretofore in connection with application Ser. No. 08/157,815 (now U.S. Pat. No. 5,505,090), such signals are supplied to the Analyzer 78 and thence to the Visual Display Unit 82 which can provide a printout of a colored contour map of the fault area, exemplified by FIGS. 6 and 7. Additionally, the essential data can be recorded by a printout system to provide a suitable graph, such as Graph C of FIG. 5.

If supporting structure such as stringers or other anomalous areas, are in the inspected structure, these will also be displayed by the graphs and Visual Display Unit 82, but since such stringers, for example, will be known and mapped for a particular structure, they can be disregarded and not confused with faults or damaged areas.

Note that relaxation frequencies and amplitudes peculiar to a particular fault condition vary not only from structure to structure but from one fault to another if the physical characteristics of the fault conditions are different. For example, a fault deep in a structure will exhibit a different spectrum of relaxation frequencies and amplitudes than will a shallower fault condition. Also the relaxation frequencies and amplitudes may vary within a particular fault condition. The computer and logic circuits described can be programmed to sense such differences, as explained above, and subtract the average background FFT and the damaged area FFTs to provide clear and unambiguous visual indications of faults in the specimen or structure under test.

While the invention has been described with reference to a particular embodiment, it will be understood that modifications in the manner of processing the FFTs to ascertain the average or statistical spectrum of fault-free areas may be made. The inventive concept of subtracting out the average or statistical spectrum, or so-called background noise, leads to greatly improved results and enables the use of the process by lesser skilled operators, since interpretation of the final displays produced is unambiguous as to damaged areas. Such areas can then be more closely scrutinized to determine the nature and extent of the damage.

We claim:

1. In a method for non-destructively inspecting for faults in or beneath the surface of a structure, in which high energy acoustic impulses are directed from a remote location sequentially onto a multiplicity of local areas on the surface of the structure for vibrationally exciting said local areas, and a beam of coherent light is synchronously directed onto the local areas and is reflected and the reflected light energy received, detecting the shifts in wavelength of the received light energy caused by out-of-plane displacement of the excited local areas, and in which the acoustic pulses and the beam of coherent light are scanned to successive local areas, and information including time domain relaxation signals is obtained representative of the local areas, the improvement comprising the steps of:

processing the time domain signals of each local area to provide FFT spectra, analyzing the FFT spectra to enable selection of desired FFTs, selecting and setting aside FFTs deviating from a predetermined standard which will be representative of damaged or other anomalous areas of the structure, selecting the remaining FFTs to provide an average or statistical FFT representative of fault-free areas of the structure, and subtracting the average and deviating FFTs to provide a resultant signal representative of damaged or other anomalous areas of the structure.

2. The method according to claim 1, wherein said method comprises the additional steps of:

generating an optical image of at least the scanned portion of the surface of the structure under inspection, and superimposing on said optical image a visual image generated by the resultant signal so that the damaged and anomalous areas can be visually identified.

3. In apparatus for non-destructively inspecting for faults in or beneath the surface of a structure, in which means are provided to direct high energy acoustic impulses from a remote location onto a multiplicity of local areas on the surface of the structure for vibrationally exciting said local areas in sequence, means for directing a beam of coherent light synchronously onto the local areas and means for receiving the light energy reflected from the local areas, means for detecting the shifts in wavelength of the received light energy caused by out-of-plane displacement of the excited local areas, means for scanning successive local areas by the acoustic pulses and the beam of coherent light, and means for obtaining information including time domain relaxation signals representative of the local areas, the improvement comprising:

means for processing the time domain signals of each local area to provide FFT spectra, means for analyzing the resultant FFTs to enable selection of desired FFTs, means for selecting and setting aside FFTs deviating from a predetermined standard and which are representative of damaged or other anomalous areas of the structure, means for selecting the remaining FFTs to provide an average or statistical FFT representative of fault-free areas of the structure, and means for subtracting the average and deviating FFTs to provide a resultant signal representative of damaged or other anomalous areas of the structure.

4. Apparatus according to claim 3, including:

means for generating an optical image of at least the scanned portion of the surface under inspection, and means for superimposing on said optical image a visual image generated by the resultant signal so that the damaged or other anomalous areas can be visually identified.

* * * * *